US007608589B2

(12) United States Patent
Thacker

(10) Patent No.: US 7,608,589 B2
(45) Date of Patent: Oct. 27, 2009

(54) PEPTIDYL DIACYLGLYCERIDES

(75) Inventor: James D. Thacker, Marietta, OH (US)

(73) Assignee: Therimunex Pharmaceuticals, Inc., Doylestown ( * ) Notice: Subject to any disclaimer, the term of this patent is extended or adjusted under 35 U.S.C. 154(b) by 446 days.

(21) Appl. No.: 11/459,772

(22) Filed: Jul. 25, 2006

(65) Prior Publication Data

US 2007/0197436 A1    Aug. 23, 2007

Related U.S. Application Data

(60) Provisional application No. 60/702,111, filed on Jul. 25, 2005, provisional application No. 60/777,319, filed on Feb. 28, 2006, provisional application No. 60/787,385, filed on Mar. 29, 2006.

(51) Int. Cl.
*A61K 38/00* (2006.01)
(52) U.S. Cl. .................. 514/14; 514/12; 514/13; 514/15; 514/16; 514/17
(58) Field of Classification Search .................. None
See application file for complete search history.

(56) References Cited

U.S. PATENT DOCUMENTS

| 5,614,414 | A | 3/1997 | Ryan et al. |
| 6,552,007 | B2 | 4/2003 | Chen et al. |
| 6,696,072 | B1 | 2/2004 | Podolski |
| 7,358,044 | B2 | 4/2008 | Thacker et al. |

FOREIGN PATENT DOCUMENTS

EP    1319667  A2    6/2003

OTHER PUBLICATIONS

Morgan et al., Approaches to the Discovery of Non-Peptide Ligands for Peptide Receptors and Peptidases, 1989, Annual Reports in Medicinal Chemistry 24: 243-252.
Ripka et al., Peptidomimetic design, 1998, Current Opinion in Chemical Biology 2:441-452.
Hruby et al., Synthesis of oligopeptide and peptidomimetic libraries, 1997, Current Opinion in Chemical Biology 1:114-119.
Hruby et al., Conformational and Topographical Considerations in Designing Agonist Peptidomimetics from Peptide Leads, 2000, Current Medicinal Chemistry 7:945-970.
Hart et al., Susceptibility to hydrophobic molecules and phospholipid composition in *Pasteruella multocida* and *Actinobacillus lignieresii*, 1988, Antimicrob. Agents Chemother. 32:1354-1359.
Fujino et al., Low-density lipoprotein receptor-related protein 5 (LRP5) is essential for normal cholesterol metabolism and glucose-induced insulin secretion, 2003, PNAS 100(1):229-234.
http://en.wikipedia.org/wiki/Low-density_lipoprotein, date Jun. 9, 2004, 1 page.
Remington's Pharmaceutical Sciences, Mack Publishing, Co., Easton, PA (TOC), date May 10, 2005, 13 pages.
Darnell et al., Variability of cell surface hydrophobicity among *Pasteruella multocida* somatic serotype and *Actinobacillus lignieresii* strains, 1987, J. Clin. Microbiol. 25:67-71.
Hancock, Peptide antibiotics,1997, Lancet 349:418-422.
Tizard, Veterinary Immunology: An Introduction, 5$^{th}$ ed., Philadelphia, PA, W.B. Saunders Company, 1996 (TOC).
Zinkl, The leukocytes, 1981, Vet. Clin. North Am. Small Anim. Pract. 11:237-263.
Latimer et al., Clinical Interpretation of leukocyte responses, 1989, Vet. Clin. North Am: Small Anim. Pract. 19:637-668.
Maxwell, Avian blood leukocyte responses to stress, 1993, Worlds Polult. Sci. J. 49:34-43.
Lucas et al., Atlas of avian hematology, 1961, United States Department of Agriculture, Agriculture Monograph 25, Washington, D.C. (TOC).
Kaisho et al., Toll-Like Receptors as Adjuvant Receptors, 2002, Biochim. Biophys. Acta 1589:1-13.
Medzhitov, Toll-Like Receptors and Innate Immunity, 2001, Nat. Rev. Immunol 1:135-145.
Hallman et al., Toll-like Receptors as Sensors of Pathogens, 2001, Pediatr. Res. 50:315-321.
Poquet et al., Expansion of Vγ9Vδ2 T Cells is Triggered by *Francisella tularensis*-Derived Phosphoantigens in Tularemia but Not after Tularemia Vaccination, 1998, Infect. Immun. 66:2107-2114.
Carding et al., γδ Cells: Functional Plasticity and Heterogeneity, 2002, Nat. Rev. Immunol. 2:336-345.
Ladel et al., Control of Natural Killer Cell-Mediated Innate Resistance against the Intracellular Pathogen Listeria monocytogenes by γ/δ T Lymphocytes, 1996, Infect. Immun. 64(5):1744-1749.
Chen et al., Adaptive immune response of Vγ2Vδ2 T cells: a new paradigm, 2003, Trends in Immunology 24:213-219.
Zuany-Amorim et al., Toll-Like Receptors as Potential Therapeutic Targets for Multiple Diseases, 2002, Nat. Rev. Drug Discov. 1:797-807.
Takeuchi et al., Toll-like receptors; their physiological role and signal transduction system, 2001, Int. Immunopharmacol. 1:625-635.
Akira et al., Toll-like receptors: critical proteins linking innate and acquired immunity, 2001, Nat. Immunol. 2:675-680.
Werling et al., Toll-like receptors linking innate and adaptive immune responses, 2003, Vet. Immunol. Immunopathol. 91:1-12.
Braun, Covalent Lipoprotein from the Outer Membrane of *Escherichia coli*, 1975, Biochem. Biophys. Acta 415:335-337.

(Continued)

*Primary Examiner*—Cecilia Tsang
*Assistant Examiner*—Marcela M Cordero Garcia
(74) *Attorney, Agent, or Firm*—Joseph F. Aceto, Esq.; James L. Wilcox, Esq.

(57) ABSTRACT

Peptide and peptides that may be covalently linked to a lipid and methods of using such peptides and lipopeptides to prevent or treat disease are disclosed herein.

15 Claims, 5 Drawing Sheets

OTHER PUBLICATIONS

Okusawa, 2004, Infection and Immunity 72:1657-1665.

Bessler et al., Induction of Lymphocyte Proliferation and membrane Changes by Lipopeptide Derivatives of the Lipoprotein from the Outer Membrane of *Escherichia coli*, 1997, Z. Immun.-Forsch. 15:11-22.

Sumida et al., Predominant Expansion of Vγ9/Vδ2 T Cells in a Tularemia Patient, 1992, Infect. Immunol. 60(6):2554-2558.

Hara et al., Predominant Activation and Expansion of Vγ9-bearing γδT Cells in Vivo as well as In Vitro in Salmonella Infection, 1992, J. Clin. Invest. 90:204-210.

Modlin et al. Lymphocytes bearing antigen-specific γδ T-cell receptors accumulate in human infectious disease lesions, 1989, Nature, 339:544-548.

Jouen-Beades et al., In Vivo and In Vitro Activation and expansion of γδ T Cells during Listeria monocytogenes Infection in Humans, 1997, Infect. Immun. 65(10):4267-4272.

Russo et al., Antigen-Reactive γδ T Cells in Human Leishmaniasis, 1993, J. Immunol. 151(7):3712-3718.

Ho et al., Increased γδ cells in acute *Plasmodium falciparum* malaria, 1990, Immunol. Lett. 25:139-141.

Hoft et al., Bacille Calmette-Guerin Vaccination enhances Human γδ T Cell Responsiveness to Mycobacteria Suggestive of a Memory-Like Phenotype, 1998, J. lmmunol. 161:1045-1054.

Mohr et al., Radical-Mediated Oxidation of Isolated Human Very-Low-Density Lipoprotein, 1994, Arterioscler. Thromb. 14:1186-1192.

PEPTIDYL DIACYLGLYCERIDES

CROSS REFERENCES AND RELATED APPLICATIONS

This application claims priority from U.S. Provisional Application No. 60/702,111 entitled "A New Class of Lipopeptides and the Biological Activities Thereof" filed Jul. 25, 2005, U.S. Provisional Application No. 60/777,319 entitled "New Immunoregulating Peptides and Lipopeptides and Their Biological Activities" filed Feb. 28, 2006, and U.S. Provisional Application No. 60/787,385 entitled "New Immunoregulating Peptides and Lipopeptides" filed Mar. 29, 2006, the disclosure of which are incorporate by reference herein in their entireties.

STATEMENT REGARDING FEDERALLY SPONSORED RESEARCH PROJECTS

Not Applicable

JOINT RESEARCH AGREEMENT

Not Applicable

INCORPORATION BY REFERENCE OF MATERIAL SUBMITTED ON DISC

Not Applicable

BACKGROUND OF THE INVENTION

Under the current paradigm, immune function in vertebrates is characterized as consisting of two major types of responses, the adaptive immune response and the innate immune response. The adaptive immune response is present only in vertebrates and provides selective long-term protection from re-infection by pathogens to which there has been a previous exposure. The innate immune response provides an immediate response to infection or injury and promotes local phagocytic, cytolytic, and cytotoxic actions of the effector cells.

The innate immune system is evolutionarily the oldest (>250 million years old) immune system in animals and is present in virtually all vertebrates and invertebrates. The innate arm of the vertebrate immune response is the first line of defense against invading pathogens and is composed of immune cells that are largely found in the tissue compartment, particularly in the tissues of the major portals of entry for bacterial and viral pathogens such as the skin and the respiratory and digestive tracts. Mediated by a set of germ-line-encoded receptors, the immune cells of the innate arm of the immune response are phenotypically and genotypically distinct from the immune cells that mediate the actions of the adaptive arm of the immune response.

The innate immune response and inflammation are intimately related. The inflammatory response to localized infection or trauma is generally regarded as beneficial resulting in pathogen containment and clearance by the cytotoxic and phagocytic actions of the tissue resident effector cells. Whereas local inflammation is beneficial, systemic inflammation is a deleterious and often fatal consequence of traumatic injury or septicemia. Thus, limiting the inflammatory response to trauma or septicemia is the subject matter of current medical research, and restricting the innate immune response during traumatic injury or septicemia may be an effective way of limiting inflammation.

The Tissue Factor or extrinsic clotting cascade has been recently identified as an activator of clotting during systemic inflammation or septicemia. Coagulation has traditionally been viewed as a separate process from inflammation that evolved specifically to prevent the loss of blood volume and blood constituents as a result of a physical breach of the circulatory system. In this traditional view, thrombin mediates the cascade that is the sole mechanism for blood coagulation. However, recent evidence has established that pro-inflammatory cytokines, particularly IL-6, also promote coagulation through increased expression of Tissue Factor (TF) which is now thought to be the principal activator of clotting during systemic inflammation or septicemia.

Conversely, Thrombin has a variety of pro-inflammatory actions to include leukocyte adhesion, pro-inflammatory cytokine production (particularly IL-6 and IL-8), soluble CD40L release from platelets, and histamine release from mast cells. Platelets, too, are previously unrecognized as inflammatory mediators with molecular signaling capabilities that link inflammation and the innate immune response. Thus, it is now clear that coagulation, inflammation, and the innate immune response are inter-related processes. The role of inflammation in the host immune response is poorly understood, yet it is an important aspect of regulation, control, and the interrelation of the innate arm of immune response. In a unified view, the mammalian innate immune response is a continuum of four stages beginning with inflammation, up regulation of the innate immune effector cells, down regulation of the cytotoxic and cytolytic actions of the innate immune response, and a return to homeostasis. A better understanding of the inflammatory cascade is central to an understanding of the immunopathology that underlies many of the most significant human diseases as well as the rational design of safe and effective therapeutic strategies.

T cells are a central player in the mammalian immune response and have been classified by the differential expression of T cell receptors (TCR) as either αβ or γδ heterodimers. The majority of circulating T cells in humans are of the αβ subset (αβT cells). Research has historically been focused on the αβ T cells, and their role in the adaptive immune response has been clearly established by their recognition of antigens via antigen presenting cells and TCR binding with the major histocompatability complex (MHC).

The γδ subset of T cells are a less well studied cell lineage of tissue resident cells encompassing up to 50% of the tissue resident T cell population. In circulation however, γδ T cells are much less prevalent than their αβ cousins and constitute only about 1-5% of the circulating T cell population. The impact of γδ T cell cytokine release on macrophage and natural killer cell (NK cell) activation has recently been reported in a murine model. Briefly, mice deficient in γδ T cell have been shown to be less able to withstand bacterial infection and are characterized by disruption of macrophage homeostasis, reduced INF-γ production from NK cells, and increased bacterial growth. Antigen recognition by γδ T cells is MHC independent and these cells have a diverse TCR repertoire. Therefore, γδ T cell can be activated during a wide variety of infections. Upon activation, these cells can undergo clonal expansion to constitute up to 97% of the total T cell population using a mechanism for clonal expansion that appears to be similar to an adaptive-type immune response in vitro.

The transcriptional profile of γδ T cells in naive mice and mice infected with *Yesernia pseudotuberculosis* has been characterized indicating that murine γδ T cells constitutively expressed high levels of transcripts for Granzymes A, B, and RANTES and other cytotoxic mediators such as lymphotoxin b, Fas ligand, NKR-PLA, NKR-PLC, LAG-3 and 2B4 as well as the corresponding inhibitory receptors. However to the best of our knowledge, similar studies have not been undertaken with primate γδ T cells.

Innate immune cell recognition of pathogens is generally thought to be mediated by a set of germline encoded receptors referred to as pattern-recognition receptors (PRRs) on tissue resident monocytes. The most well studied PRR are the Toll-like receptors (TLR). Toll receptors are transmembrane receptors first identified in *Drosophila*, but a homologous family of TLRs was subsequently identified in humans. The intracellular domain of the TLRs is structurally closely related to the IL-1 receptor and is referred to as the Toll/interleukin-1 (TIR) domain. *Drosophila* Toll and human TLR share homologous intracellular signaling components consisting of four major components: (1) the adaptor proteins MyD88, (2) TOLLIP (Toll-interacting protein), (3) the protein kinase IRAK (IL-IR-associated kinase), and (4) TRAF6 (TNF receptor-associated factor 6).

TLRs recognize conserved regions of pathogen derived molecules, commonly referred to as pathogen-associated molecular patterns or PAMPs, such as bacterial cell wall lipopolysaccharide (LPS), *Staphylococcus* enterotoxin B (SEB), tetanus toxin antigen (TTA), double stranded viral RNA fragments, bacterial DNA, and flagellin. TLR activation ultimately leads to activation of NFκB and downstream chemokine production in macrophage and dendritic cells including IL-8, IP-10, MIP-1α and β, and RANTES, as well as an influx of NK cells and T cells at the site of infection. Other than fibronectin fragments, human TLRs have not been shown to recognize endogenous ligands in response to pathogen infection in a manner that is analogous to the *Drosophila* Spätzle processing.

Heat shock proteins (HSPs) are a highly conserved family of stress-induced proteins that are produced by mammalian cells and microbial pathogen alike, and HSPs have been implicated in the immunopathology of rheumatoid arthritis and atherosclerosis. The immunogenicity of the HSPs appears to be derived from antigenic peptides chaperoned by the HSPs. HSP-peptide complexes potentiate the antigenicity of the chaperoned peptides by several orders of magnitude as compared to a non-HSP peptide binding antigen such as albumin. A common receptor for the HSP-peptide complex has been identified as CD91, an $\alpha_2$ macroglobulin receptor on monocytes. Thus, the HSPs are an important inflammatory regulator protein in the innate immune response to pathogen infection.

Defensins and cathelicidins are small cationic anti-bacterial peptides with immunoregulatory properties that have recently been discovered. Human defensins and cathelicidins are derived from cells including neutrophils, monocytes, certain lymphocyte populations, keratinocytes, and bronchial epithelial cells. Defensins are 3,5-4 kDa cysteine-rich, cationic peptides that have an intricate tertiary structure that resembles the structure of chemokines. Cathelicidins are linear peptides, as exemplified by LL-37, derived from the C-terminal sequence of human CAP-18.

Various lipoproteins derived from bacterial cell membranes have been shown to activate macrophages, fibroblasts, and lymphocytes to induce an inflammatory response and are broadly considered to be pro-inflammatory in nature. For instance a lipoprotein from *Escherichia coli* has been characterized and was shown to be an activator of monocytes. Recently, a family of lipopeptides has been characterized from *Mycoplasma* organisms. The parent 2 kDa lipopeptide has been characterized as a potent activator of macrophages and is known as the macrophage activating lipopeptide i.e., MALP-2. These monocyte activating lipopeptides have certain key structural features in common. The mycoplasmal lipopeptides contain peptides of varying lengths and sequences, but all have an N-terminal cysteine. The lipid portion is esterified as a 2,3-diacoyloxypropyl thioether of the N-terminal cysteine. Thus, the N-terminal nitrogen is free. Further, the S-enantiomer is biologically active whereas the R-enantiomer is not. The active lipopetide derived from *E. coli*, on the other hand, is a tri-lipid variant wherein the third lipid is attached as an N-terminal amide.

The biological role of the diacylglycerols has been well described in the literature. For instance it is well known that diacylglycerols participate in the transport of lipids as triglycerides and in association with soluble proteins such as the apolipoproteins, are transporters of cholesterol. Diacylglycerols are also known to have an intracellular signaling function. Intracellular, membrane bound phosphatidyl inositol-4, 5-biphosphate is cleaved by the actions of the enzyme phospholipase C to release two intracellular messenger molecules, inositol triphosphate and membrane bound diacylglycerol (specifically 1-stearoyl-2-arachidonoyl glycerol). Diacylglycerol activates protein kinase C which activates transcription factor NFκB to up regulate the gene expression of various cytokines and chemokines.

SUMMARY OF THE INVENTION

Embodiments of the invention described herein include compounds that may stimulate an immune response that include an immuno-reactive peptide of from about 5 to about 25 amino acids covalently linked to a lipid. In some embodiments, the lipid may be a glyceride of general formula (I):

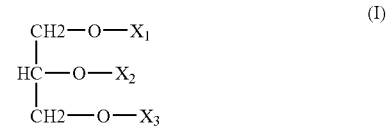

wherein $X_1$, $X_2$ and $X_3$ are selected from hydrogen, $C_2$ to $C_{25}$ fatty acid and a peptide, and at least one of $X_1$, $X_2$ and $X_3$ is a peptide. The fatty acid of embodiments may be saturated, unsaturated, or poly unsaturated fatty acids, and the peptide may be covalently linked to the lipid by a ester bond at the C-terminus of the peptide.

In certain embodiments, the immuno-reactive peptide is of amino acid sequence XSHNLCX (SEQ ID NO: 1) or inversions thereof and, in some embodiments, may be RSHNLCX (SEQ ID NO: 2) or YTSHNLCX (SEQ ID NO: 3) or inversions thereof. In still other embodiments, the amino acid sequence may be YTSHNLCXCLNHSR (SEQ ID NO: 4) or inversions thereof, and on certain other embodiments, the amino acid sequence may be FNNFTVSFWLRVP-KVSASHLE (SEQ ID NO: 5).

Compounds of embodiments of the invention may further contain a pharmaceutically acceptable excipient and may be provided in a unit dose form that is consistent with an effective amount of the compound, and these embodiments may be considered pharmaceutical compositions.

Further embodiments of the invention, include methods which may include administering an effective amount of an agent made up of a peptide having about 5 to about 25 amino acids covalently linked to a lipid to a subject in need thereof, and stimulating an immune response. The peptide, of embodiments of the invention, may include a peptide or peptide fragment of amino acid sequence RSHNLCX (SEQ ID NO: 2)or YTSHNLCX (SEQ ID NO: 3or inversions thereof and, in some embodiments, YTSHNLCXCLNHSR (SEQ ID NO: 6)or inversions thereof.

Agents of embodiments of the invention may include a glyceride of general formula (I)

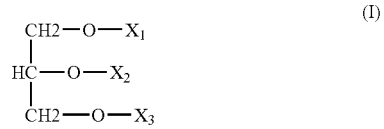

wherein $X_1$, $X_2$ and $X_3$ are selected from hydrogen, $C_2$ to $C_{25}$ fatty acid and a peptide, and a least one of $X_1$, $X_2$ and $X_3$ is a peptide. The fatty acid of embodiments may be saturated, unsaturated, or poly unsaturated fatty acids. The peptide may be covalently linked to the lipid by a ester bond at the C-terminus of the peptide. The agent may be administered to stimulate an innate immune response, and tissue resident immune cells including, but not limited to, γδ T cells, monocytes, NK cells, neutrophils, CD5+ B-cells and combinations thereof may be stimulated. In some embodiments, the tissue resident immune cells are stimulated when contacted by the peptide.

The immune response stimulated, in certain embodiments of the invention, may include stimulating an immune response for at least 3 days following administration of the agent, and in certain other embodiments, the immune response may be stimulated for a week or more.

In still other embodiments of the invention, the agent may be deposited in fatty tissue of the subject, and the agent may be administered by any method including enteral, parenteral, and topical delivery, mammary infusion, and combinations of these. Parenteral administration may include, but not limited to, intra-articular, intrasynovial, interaathecal, intraarterial, intraveinous, intramuscular, subcutaneous and combinations thereof. Enteral administration may include, but not limited to, oral, peroral, rectal and combinations thereof, and topical administration may include, but not limited to, intranasal, intrarespiratory, epicutaneous, transdermal delivery and combinations thereof.

In some embodiments of the invention, the agent may be administered prior to exposure to a disease forming agent and may, in these embodiments, substantially prevent disease. In other embodiments, the agent may be administered prior to disease. The agent may also be delivered following exposure to a disease forming agent and may, in these embodiments, may substantially prevent disease. In yet further embodiments, the agent may be delivered to the subject following disease.

Further methods of embodiments of the invention include methods for treating an infection, methods for stimulating an immune response, methods for preventing disease, methods for preventing an infection, and combinations of these such as methods of treating a disease and preventing a secondary infection using agents and compositions of the invention described hereinabove.

Embodiments of the invention further include antibodies directed to compounds of the invention, and methods of treating inflammation such as, but not limited to, systemic inflammation, chronic inflammatory disease, and inflammation due to sepsis, non-septic injury, trauma, surgery or combinations thereof by administering the antibodies of embodiments of the invention. Antibodies of embodiments of the invention may be administered to a subject by any method known in the art including, but not limited to, enteral, parentaral, and topical delivery.

Antibodies of embodiments of the invention may also be linked to a selectable marker such as, but not limited to, a fluorescent marker such as a protein, or a quantum dot to make a probe, and methods of using such probes to detect and identify peptides in a sample, such as a biological, cell or tissue sample and cells or proteins that interact with such peptides.

DESCRIPTION OF THE INVENTION

Figure 1:
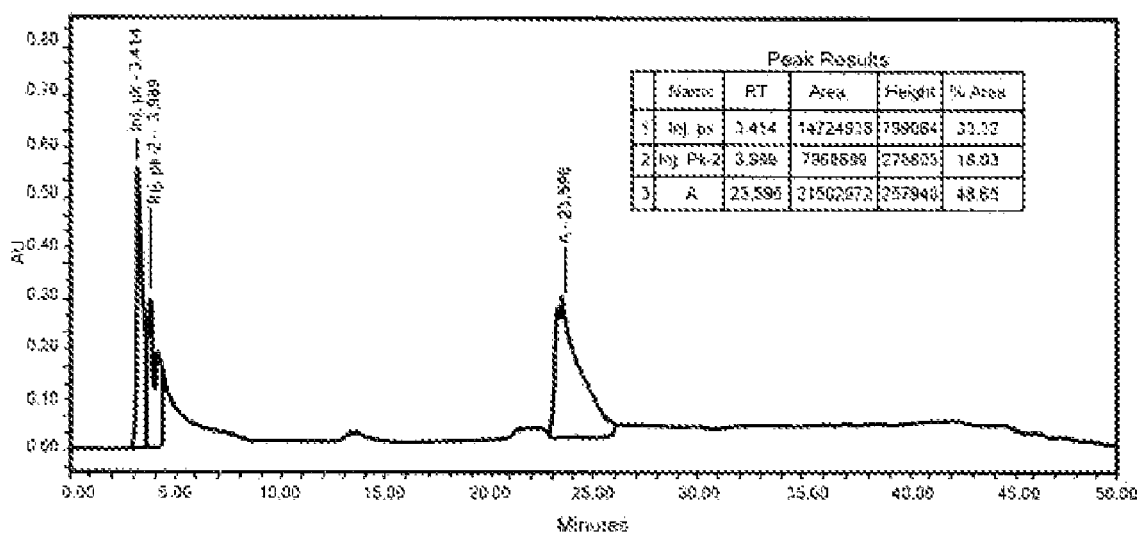
FIG. 1 shows a representative HPLC chromatogram of purified 1-peptidyl-2,3-diacylglyceride.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and material similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

An "adjuvant" refers to any substance which enhances the immune-stimulating properties of an antigen or the pharmacological effect of a drug.

As used herein, the term "about" means plus or minus 10% of the numerical value of the number with which it is being used. Therefore, about 50% means in the range of 45%-55

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

As used herein, the term "pharmaceutically acceptable salts, esters, amides, and prodrugs" refers to those carboxylate salts, amino acid addition salts, esters, amides, and prodrugs of the compounds of the present invention which are, within the scope of sound medical judgment, suitable for use in contact with the tissue of patients without undue toxicity, irritation, allergic response, and the like, commensurate with a reasonable benefit/risk ratio, and effective for their intended use, as well as the zwitterionic forms, where possible, of the compounds of the invention.

As used herein, the term "physiologically tolerable" and grammatical variations thereof, as they refer to compositions, carriers, diluents and reagents, are used interchangeably and represent that the materials are capable of administration upon a mammal without or with minimal production of undesirable physiological effects such as nausea, dizziness, rash, or gastric upset. In a preferred embodiment, the therapeutic composition is not antigenic when administered to a human patient or other animal for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted.

As used herein "subject" or "patient" refers to an animal or mammal including, but not limited to, human, dog, cat, horse, cow, pig, sheep, goat, chicken, monkey, rabbit, rat, mouse, etc.

"Disease" for purposes of the present invention may be any infectious agent such as, for example, viral particles, bacterial pathogens, and the like. "Disease" as used in reference to a "diseased subject" may refer to any human or animal subject infected with an infectious agent. The "diseased subject" may or may not exhibit signs of infection such as, for example, known symptoms.

As used herein a "sample" includes a biological sample which can be tested by the methods of the present invention and include, but are not limited to, body fluids such as serum, plasma, whole blood, cerebrospinal fluid, lymph fluids, various external secretions (urine, respiratory, intestinal or genitourinary tract secretions, tears, etc.), etc.

As used herein, the term "therapeutic" means an agent utilized to treat, combat, ameliorate, prevent or improve an unwanted condition or disease of a patient. Embodiments of the present invention are directed to stimulate the innate immune response or modulation of the inflammatory response. The methods herein for use contemplate prophylactic use as well as curative use in therapy of an existing conditions.

The terms "therapeutically effective" or "effective", as used herein, may be used interchangeably and refer to an amount of a therapeutic composition embodiments of the present invention—e.g. one or more of the peptidyl diacylglycerides or mimetics thereof. For example, a therapeutically effective amount of a composition comprising 1-peptidyl-2,3-diacylglyceride, or mimetics thereof, is a predetermined amount calculated to achieve the desired effect, i.e., to effectively stimulate an innate immune response in an animal to whom the composition is administered.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., excipient, carrier, or vehicle.

One embodiment of the present invention may be directed to a 1-peptidyl-2,3-diacylglyceride or PDAG. Other embodiments of the invention may include compositions containing PDAGs, compositions that contain portions of PDAGs, compositions containing analogs of PDAG peptides and compositions containing peptide mimetics of PDAGs.

In embodiments of the invention, PDAGs, portions of PDAGs, analogs of PDAGs and mimetics of PDAGs may be provided to a subject and may stimulate therapeutic effects such as, but not limited to, inducing an immune response, and in certain embodiments, the immune response may be an innate immune response in the subject so provided. PDAGs, portions of PDAGs, analogs of PDAG and mimetics of PDAG, in other embodiments of the invention, may be administered to a subject undergoing treatment for disease, to a subject that is healthy, or to a subject that is healthy and may be exposed to disease, disease forming particles, or diseased humans and/or animals. In embodiments of the invention where PDAGs, portions of PDAGs, analogs of PDAGs and mimetics of PDAGs, and therapeutics containing PDAGs, portions of PDAGs, analogs of PDAGs and mimetics of PDAGs are provided to a subject that is healthy, the PDAGs, portions of PDAGs, analogs of PDAGs and mimetics of PDAG may promote the prophylactic activation of the immune system of the subject, and in certain embodiments prophylactic activation of innate immunity.

Without wishing to be bound by theory, the PDAGs, portions of PDAGs, analogs of PDAGs and mimetics of PDAGs, in embodiments of the invention, when provided to a subject may activate tissue resident immune cells in the subject. In some embodiments, the PDAGs, portions of PDAGs, analogs of PDAGs and mimetics of PDAGs may initiate an immune response, and in other embodiments, the immune response may be an innate immune response.

Embodiments of the present invention may also include methods of administering PDAGs, portions of PDAGs, analogs of PDAGs and mimetics of PDAG and therapeutics containing PDAGs, portions of PDAGs, analogs of PDAGs and mimetics of PDAGs such as, but not limited to, parenteral, enteral, or topical administration.

Other embodiments of the present invention include antibodies with specificity for the PDAGs, and methods for the use of such antibodies in depleting systemic or localized concentrations of PDAGs in a subject. In certain embodiments, the subject provided with antibodies specific to PDAGs may exhibit symptoms of immune disease such as, but not limited to, systemic inflammation, chronic inflammatory diseases, atherosclerotic disease, rheumatoid diseases, autoimmune diseases, and the like.

Still other embodiments of the invention include fluorescently labeled PDAGs, analogs of PDAGs, and fluorescently labeled antibodies or antibody fragments with specificity to PDAGs and methods for producing such fluorescently labeled PDAGs, analogs of PDAGs and antibodies. Fluorescently labeled PDAGs, analogs of PDAGs and antibodies may be used, in embodiments of the invention, as diagnostic tools to assess aspects of the immune system and immunopathology both in vitro and in vivo, and in some embodiments, subjects may include, but not limited to, subject exhibiting symptoms consistent with chronic inflammatory disease, autoimmune disease, atherosclerotic disease, diabetes and the like.

PDAGs described in various embodiments of the invention may include a peptidyl diacylglyceride having at least one peptide moiety covalently attached to a lipid moiety and are of the general formula 1-peptidyl-2,3-diacylglyceride. In certain embodiments, the lipid moiety is 1-stearoyl-2-arachidonoyl glycerol.

The PDAGs described in the embodiments of the invention may be of general formula(I):

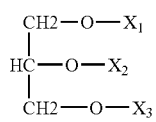

where $X_1$, $X_2$ and $X_3$ may be hydrogen, a peptide, peptide mimetic, or peptide analog, or a saturated, unsaturated, or polyunsaturated fatty acid having from about 1 to about 20 carbon atoms. In some embodiments of the invention, at least one of $X_1$, $X_2$ and $X_3$ may be a peptide, peptide mimetic, or peptide analog, and in others, more than one of $X_1$, $X_2$ and $X_3$ may be a peptide, peptide mimetic, peptide analog.

The peptide moiety of embodiments of the present invention may be made up of from between about 5 to about 25 amino acids and may include one or more naturally occurring, non-naturally occurring and chemically modified amino acids. These peptide moieties may weigh from about 1000 to about 3000 amu. Peptides encompassed by the present invention or mimetics thereof may include any amino acid sequence that confers the desired effect of activating immunity. Peptide moieties may be made and/or isolated prior to being attached to the lipid moiety and may be synthesized and isolated from a natural source such as, for example, human, animal, bacterium sources and the like or may be synthesized by any method known in the art. Peptides, peptide mimetics and peptide analogs so synthesized and isolated may be purified or concentrated by methods known to those of ordinary skill in the art such as, for example, by filtration, chromatography and the like. The peptide moiety may be covalently conjugated to the lipid moiety by esterification at the carboxy terminal carboxylic acid of the peptide, and in some embodiments, the peptide moiety may be conjugated to the lipid moiety through a phosphoester at the carboxy terminal carboxylic acid of the peptide.

Peptides, peptide mimetics, or peptide analogs that are covalently conjugated to a lipid moiety to make up PDAGs may be considered and will hereinafter be referred to as "PDAG lipopeptides".

For example, PDAGs may be synthesized as follows. PDAG peptides or PDAG peptide mimetics may be made using solid-phase synthetic methods such as, for example, an FMOC synthesis protocol with extended HBTU/HOBt coupling cycles and pre-loaded Wang resins. Following synthesis, the peptide side chain protective groups may be cleaved and the peptide may be released from the resin with Reagent-K. The peptide may then be extracted from synthesis buffers using for example diethyl ether extraction and lyophilization. Reversed phase C-18 purification may be used to further purify the resultant crude peptides and may be followed by MALDI-TOF characterization to confirm the amino acid sequence.

The PDAG peptide of peptide mimetic may be covalently attached to the lipid portion of the PDAG using a two step process wherein, first, the PDAG peptide is synthesized as described above but without the de-protection step. The C-terminal carboxylic acid may then be activated with, for example, dicyclohexylcarbimide, and the peptide may be incubated in the presence diacylglycerol or a diacylglycerol phosphate for several hours. Esterification of the may occur during the incubation step allowing a peptidyl diacylglyceride to form. The peptide side chain protective groups may then be cleaved with Reagent-K, and the peptidyl diacylglyceride product may be isolated and purified by chromatography. MALDI-TOF characterization may then be used to confirm the structure of the purified product.

The peptide portion of PDAGs of embodiments of the present invention may be modified such as, for example, by replacement of one or more of the naturally occurring side chains of the 20 genetically encoded amino acids (or D amino acids) with non-naturally occurring side chains, examples of non-naturally occurring side chains include, but are not limited to, alkyl, lower alkyl, 4-, 5-, 6-, to 7 membered alkaryl, amide, amide lower alkyl, amide di (lower alkyl), lower alkoxy, hydroxy, carboxy and the lower ester derivatives thereof, and with 4-, 5-, 6-, to 7 membered heterocyclics to produce peptide mimetics. For example, proline analogs may be made in which the ring size of the proline residue is changed from 5 members to 4, 6, or 7 members. Cyclic groups may be saturated or unsaturated, and if unsaturated, may be aromatic or nonaromatic. Heterocyclic groups can contain one or more heteroatom such as for example nitrogen, oxygen, and/or sulphur and the like and may form groups including, but not limited to, the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups may be substituted or unsubstituted. Substituted heterocyclic groups may contain substituents such as but not limited to alkyl, alkoxy, halogen, oxygen, or substituted or unsubstituted phenyl. Peptidomimetics of PDAG peptides may also have amino acid residues that have been chemically modified for example by phosphorylation, sulfonation, biotinylation and the like.

A variety of techniques are available for constructing peptide mimetics with the same or similar desired biological activity as the corresponding native peptide but with better solubility, stability, and/or susceptibility to hydrolysis or protcolysis. Therefore, these characteristics of peptidomimetic compounds encourage their use in therapeutic applications since they may have increased cell permeability, greater affinity and/or avidity for cell receptors and prolonged biological half-life. Certain peptidomimetic compounds are based upon the amino acid sequence of the peptides of the invention. Often, peptidomimetic compounds are synthetic compounds having a three-dimensional structure (i.e., a "peptide motif") based upon the three-dimensional structure of a selected peptide. The peptide motif provides the peptidomimetic compounds with the desired biological activity, i.e., enhancing or stimulating an immune response, wherein the binding activity of the mimetic compound is not substantially reduced, and is often the same as or greater than the activity of the native peptide on which the mimetic is modeled.

Peptidomimetic design strategies are readily available in the art. One class of peptidomimetic contains a backbone that is partially or completely a non-peptide, but mimics the peptide backbone atom-for atom and comprises side groups that likewise mimic the functionality of the side groups of the native amino acid residues. Several types of chemical bonds, such as ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics is a small non-peptide molecule that binds to another peptide or protein, but which is not necessarily a structural mimetic of the native peptide. Yet another class of peptidomimetics has arisen from combinatorial chemistry and the generation of massive chemical libraries. These generally are novel templates which, though structurally unrelated to the native peptide, possess necessary functional groups positioned on a non-peptide scaffold to serve as "topographical" mimetics of the original peptide.

Without wishing to be bound by theory, PDAGs, portions of PDAGs, analogs of PDAGs, or mimetics of PDAGs may be activated within a target tissue when lipoprotein lipase cleaves the lipid backbone of the PDGA releasing the peptidyl portion from the diacylglycerol. The peptidyl moiety may then bind to tissue resident immune cells, such as, but not limited to, γδ T cells, initiating the release of cytokines such as, but not limited to, INF-γ, TNF-α, Granzyme, and RANTES activating tissue resident macrophages, phagocytic NK cells or neutrophils and stimulating the release of other stimulatory cytokines and peptides. Cytokine release may also stimulate $CD5^4$ B-cells (also known as tissue resident B1 cells) to produce immunoglobulin (IgM, a potent opsonizing immunoglobulin) and other B-cell derived cytokines and chemokines. Therefore, embodiments of the present invention include PDAG peptides, portions of PDAG peptides, analogs of PDAG peptides and peptide mimetics of PDAG peptides that when administered to a subject may be present in a target tissue in an inactive form (i.e. covalently attached to the lipid moiety) and activated by the action of lipoprotein lipase over time thereby allowing for the maintenance of increased PDAG peptide concentrations and immuno-activation in the target tissue of the subject over time. The sustained release of active PDAG peptide may allow for sustained innate immune system activation thereby conferring the prophylactically treated subject with an enhanced ability to fight disease when immunologically challenged over time or the therapeutically treated subject with a long acting formulation of the PDAG.

In further embodiments of the present invention, more than one PDAG peptide may be covalently conjugated to the lipid moiety. Without wishing to be bound by theory, the duration of the effective release of PDAG peptide, or peptide mimetics, may be directly related to the number of PDAG peptides, or peptide mimetics, conjugated to the lipid moiety. Therefore, administration of PDAGs, portions of PDAGs, analogs of PDAGs, or mimetics of PDAGs having three PDAG peptide moieties conjugated to a single lipid moiety may release PDAG peptide over a longer period of time than a similarly administered PDAGs, portions of PDAGs, analogs of PDAGs, or mimetics of PDAGs having only one PDAG moiety conjugated to a lipid moiety.

In some embodiments, PDAGs, portions of PDAGs, analogs of PDAGs and mimetics of PDAGs may be delivered directly to a subject, and in others, PDAGs, portions of PDAGs, analogs of PDAGs and mimetics of PDAGs may be combined with a pharmaceutically-acceptable carrier to make a pharmaceutical composition that may be delivered or provided to a subject.

A variety of administration routes are available in embodiments of the invention. The particular mode selected will depend upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous, intramuscular, or infusion. Intravenous, subcutaneous, or intramuscular routes are particularly suitable for purposes of the present invention.

Pharmaceutical compositions of embodiments of the invention may include buffering agents such as, for example, acetic acid in a salt, citric acid in a salt, boric acid in a salt, phosphoric acid in a salt and the like and, optionally, preservatives, such as: benzalkonium chloride, chlorobutanol, parabens, thimerosal and the like.

Pharmaceutical compositions may conveniently be presented in unit dosage form and may be prepared by any of the methods well known in the art of pharmacy. All methods may include the step of bringing the active agent into association with a carrier that constitutes one or more accessory ingredients. In general, the compositions may be prepared by uniformly and intimately bringing the active compound into association with a liquid carrier, a finely divided solid carrier, or both, and then, if necessary, shaping the product.

Various other carrier materials may also advantageously be present in a nasal spray in appropriate quantities. The solution may be made mildly saline, by dissolving a small amount of sodium chloride in the aqueous medium. The salt concentration may be in the range of about 0.1-2.0% and will preferably be on the order of about 0.65%. Other materials such as surfactants, vitamins and vitamin derivatives, antihistamines, wetting agents, preservatives, moisturizers, emulsifiers, odorants and the like may also be present in conventional concentrations. Numerous disclosures of suitable materials may be found in the literature, along with descriptions of efficacious concentrations in aqueous media. Those skilled in the art will have no difficulty in determining suitable materials and concentrations for their known functions. Delivery of the spray to the nasal cavity may be by any conventional spray technique or device.

Embodiments of the invention also provide compositions suitable for parenteral administration wherein a sterile aqueous preparation of PDAGs, portions of PDAGs, analogs of PDAGs and mimetics of PDAGs is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid may be used in the preparation of injectables. Carrier formulation suitable for oral, subcutaneous, intravenous, intramuscular, and the like administrations can be found in Remington's Pharmaceutical Sciences, Mack Publishing Co., Easton, Pa. which is hereby incorporated by reference in its entirety.

Delivery systems of embodiments of the invention may be designed to include time-released, delayed release or sustained release delivery systems. PDAGs, portions of PDAGs, analogs of PDAGs and mimetics of PDAGs may also be used in conjunction with additional immunostimulatory or immunoenhancing agents. Using such systems, repeated administrations of PDAGs, portions of PDAGs, analogs of PDAGs and mimetics of PDAGs may by avoided increasing convenience to the subject, and may be particularly suitable for certain compositions of the present invention.

PDAGs, portions of PDAGs, analogs of PDAGs, mimetics of PDAGs and pharmaceutical compositions including PDAGs, portions of PDAGs, analogs of PDAGs and mimetics of PDAGs may be administered in an effective amount that enhances or stimulates an immune response, and in certain embodiments, in an effective amount to stimulate an innate immune response.

In general, routine experimentation in clinical trials may be used to determine specific ranges for optimal effect for each agent or pharmaceutical composition and administrative protocol. Administration of PDAGs, portions of PDAGs, analogs of PDAGs, mimetics of PDAGs and pharmaceutical compositions including PDAGs, portions of PDAGs, analogs of PDAGs and mimetics of PDAGs to specific subjects may be adjusted to within effective and safe ranges depending on the subject's condition and responsiveness to initial administrations. However, the ultimate administration protocol may be regulated according to the judgement of the attending clinician considering such factors as age, condition and size of the subject, the potency of the PDAGs, portions of PDAGs, analogs of PDAGs, mimetics of PDAGs and pharmaceutical compositions including PDAGs, portions of PDAGs, analogs of PDAGs and mimetics of PDAGs, the duration of the treatment and the severity of the disease being treated.

In embodiments of the invention, a dosage regimen of PDAGs, portions of PDAGs, analogs of PDAGs, mimetics of PDAGs and pharmaceutical compositions including PDAGs, portions of PDAGs, analogs of PDAGs and mimetics of PDAGs may be administered by nasal spray or an inhaler. For nasal spray or inhaler formulations, the ground particle size for effective dissolution or dispersion of the PDAGs, portions of PDAGs, analogs of PDAGs, mimetics of PDAGs and pharmaceutical compositions including PDAGs, portions of PDAGs, analogs of PDAGs and mimetics of PDAGs may be on the order of about 0.1 to about 20 microns, about 0.2 to about 10 microns, and in certain embodiments, about 0.2 to about 5 microns. Incorporation of PDAGs, portions of PDAGs, analogs of PDAGs, or mimetics of PDAGs into an aqueous carrier may be aided by first dispersing the PDAGs, portions of PDAGs, analogs of PDAGs, or mimetics of PDAGs in a solution such as, for example, a 4% concentration in a lactone solution. Once thoroughly mixed, dispersed, and/or dissolved, PDAGs, portions of PDAGs, analogs of PDAGs, or mimetics of PDAGs may be present at a concentration of from about 0.001% to about 2.0%, about 0.01% to about 0.35%, and in certain embodiments, about 0.10%. (All percentages herein are by weight unless otherwise noted.)

In other embodiments, PDAGs, portions of PDAGs, analogs of PDAGs, or mimetics of PDAGs may be administered orally to achieve total blood levels in the range of from about 25 µg to about 2000 µg/day, about 25 to 500 µg/day, or in certain embodiments, from about 50 to about 250 µg/day, in from two to four divided doses. In some embodiments, intermittent therapy (e.g., one week out of three weeks or three out of four weeks) may be used.

In the event that a response in a subject is insufficient at the initial doses applied, higher doses (or effectively higher doses by a different, more localized delivery route) may be employed to the extent that the patient tolerance permits. Multiple doses per day may be used to achieve appropriate systemic levels of compounds. Generally, a maximum dose may be used. A maximum dose may be considered the highest safe dose according to sound medical judgment. Those of ordinary skill in the art will understand, however, that a subject may insist upon a lower dose or tolerable dose for medical reasons, psychological reasons or for virtually any other reason.

In other embodiments of the invention, at least one PDAG, portions of PDAG, analogs of PDAG, mimetics of PDAG, or PDAG peptide may be covalently attached to an antigenic peptide or simply mixed with the antigenic peptide or vaccine prior to administration of the antigenic peptide or vaccine to a subject. Without wishing to be bound by theory, the addition of PDAG or a PDAG peptide may enhance the immunogenicity of the antigenic peptide or vaccine by stimulating the innate immune system at the time of administration of the antigenic peptide or vaccine. Synthetic antigens having covalently attached one or more PDAG or PDAG peptide or PDAG or PDAG peptide antigen or vaccine admixtures may be administered to a subject to induce a long-term adaptive, more specifically $T_H1$ type "cellular", immune response in the subject.

In further embodiments of the invention, antibodies may be raised to naturally occurring PDAGs and PDAG peptides, and in still further embodiments, antibodies so raised may be administered to a subject to deplete the concentration of the PDAG to which the antibody was raised. Without wishing to be bound by theory, administration of PDAG and/or PDAG peptide depleting antibodies may be a beneficial therapeutic strategy for subjects exhibiting uncontrolled systemic inflammation such as, for example, sepsis, atherosclerosis, rheumatoid diseases, autoimmune diseases, inflammatory bowel disease. Type II diabetes and the like. In similar embodiments, PDAG and PDAG peptide depleting antibodies may be used to treat non-septic injury such as, for example, trauma, inflammation due to extensive surgical procedures and the like.

Antibodies to PDAG and PDAG peptides, of embodiments of the invention, may be raised in rabbits, mice, goats, horses, or other species by methods well known to those skilled in the art. For example, monoclonal antibodies to PDAG or PDAG peptides may be raised utilizing the hybridoma fusion techniques, and selected hybridomas may be maintained in cell culture or in a bioreactor for the continuous production of monoclonal antibodies. In some embodiments, the PDAG peptide specific binding region of a monoclonal antibody may be selectively produced by specific chemical cleavage of the whole antibody or recombinant methods known in the art. In other embodiments, the specific PDAG binding region may be conjugated to the Fc region of a human antibody to produce a humanized chimera for administration of a PDAG depleting antibody to human subjects. Chimeric antibodies are well known in the art and may be produced using synthetic, semi-synthetic, or recombinant methods. Humanized PDAG chimera antibodies may be advantageous for use in human subjects since substantially no secondary antibody reaction in human subject may be caused.

In still other embodiments of the invention, fluorescently labeled PDAGs, PDAG peptides, or PDAG antibodies may be made. In such embodiments, fluorescent dyes such as, but not limited to, phycoerythrin (PE), a red fluorescing dye, and fluorosceinisothiocynate (FITC), a green fluorescing dye, may be activated conjugated to the N-terminus of the peptidyl portion of PDAG, PDAG peptide, or a free amino group of a PDAG antibody.

Methods for making such conjugates are well known in the art for example, a PDAG or PDAG peptide may be conjugated to a fluorescent dye through its N-terminus by activating the peptide by attaching a thiol reactive extended-chain analogue of succinimidyltrans-4-(maleimidylmethyl)cyclohexane-1-carboxylate(LC-SMCC) and separating unreacted LC-SMCC from the derivatized PDAG peptide by size exclusion chromatography. The pyridyldisulfide derivative of R-PE or FITC to the free thiol may by activated by incubating the R-PE or FITC for 10 to 15 minutes in tris-(2-carboxyethyl)phosphine (TCEP). The purified LC-SMCC-PDAG peptide derivative may then be combined with activated R-PE or FITC and mixed at 4° C. overnight. The reaction may be stopped by the addition of N-ethylmaleimide (NEM) which caps any remaining thiol groups. The R-PE or FITC-PDAG conjugate may be purified by size exclusion chromatography and lyophilized to yield the final product.

In other embodiments of the invention, fluorescently labeled PDAGs or PDAG peptides may be used to analysis tissue samples. For example, fluorescently labeled PDAGs or PDAG peptides may be mixed ex vivo with samples of a subject to detect and quantitate immune cells engaging the fluorescently labeled PDAGs or PDAG peptides. In still other embodiments, fluorescently labeled antibodies to the PDAGs or PDAG peptide may be used to detect and quantitate the levels of PDAG or PDAG peptide in ex vivo samples from subjects using methods such as fluorescent microscopic methods, FLISA and the like. Such methods of analysis are well known to those practiced in the art.

EXAMPLE 1

This example describes the isolation and structural analysis of PDAGs from human, non-human primate, and non-primate species. PDAGs may be routinely isolated in research scale quantities from the serum fraction of coagulated blood by dialysis against distilled water through a 10 kDa molecular weight cut-off dialysis cassette (Slide-A-Lyzer, Pierce Biotechnology, Inc.) and concentration by in vacuo evaporation and lyophilization of the dialysate.

The crude serum fraction is further purified by size exclusion chromatography or filtration by passage through a size exclusion resin or filter to remove salts and other low molecular weight contaminants. Final purification is accomplished by reversed phase HPLC. This procedure provides sufficient material after purification to conduct biological activity studies and initiate the chemical characterization of the bioactive component(s). LC/MS analysis characterizes the PDAG component as a 2-3 kDa lipopeptide. Quantitative analysis based upon the total mass abundance indicates that PDAG purity is >98% after HPLC. MALDI-TOF mass spectrometry may be used to confirm the amino acid sequence of the peptide and identify the lipid portion of the PDAGs. A representative HPLC profile of purified non-primate PDAG is depicted in FIG. 1. Analytical HPLC was performed using a Phemomenex C-18 column (250 ×4.6 mm) and a mobile phase 0.1% aqueous TFA (solvent A) and acetonitrile in 0.1% aqueous TFA (solvent B). A linear gradient was formed starting from 95% A and 5% B to 70% A and 30% B over 10 minutes (2.5% per minute) and then to 40% A and 60% B over the next 30 minutes (1% per minute). Under these conditions the PDAGs from human, monkey, and non-primate serum elute at 24.2 minutes, 22.7 minutes, and 23.6 minutes respectively.

Approximately 100 mg of the HPLC purified non-primate PDAG was subjected to either acid (6N HCL) or base (1N NaOH) hydrolysis and analyzed by HPLC-MS. The observed ion fragments support the presence of a stearoyl-arachidonoyl glycerol and are presented in the following table.

TABLE 1

Key Ion Fragments Supporting Identification of the Diacylglycerol

| Ion Fragments | Identity |
| --- | --- |
| PDAG Serum Fraction | |
| 875-494 | Arachidonoyl Glycerol |
| 1635-1254 | Arachidonoyl Glycerol |
| 628 | Stearoyl-Arachidonoyl Glycerol |
| Base Hydrolysis | |
| 360 | Stearoyl Glycerol |
| Acid Hydolysis | |
| 1875-1247 | Stearoyl-Arachidonoyl Glycerol |

Figure 2A:
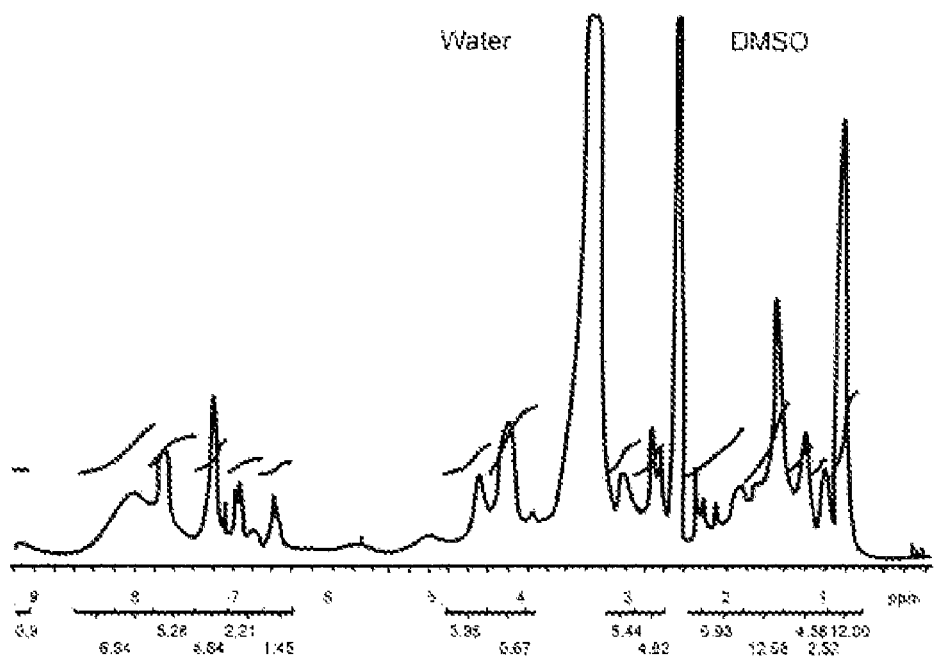
FIG. 2 shows a $^1$H nuclear magnetic resonance spectrum of HPLC purified PDAG (FIG. 2A) compared to the predicted NMR of a hypothetical 1-peptidyl-2,3-diacylglyceride (FIG. 2B). The insert shows the actual NMR spectrum of 1-stearoyl-2-arachidonoyl glycerol.
Figure 2B:
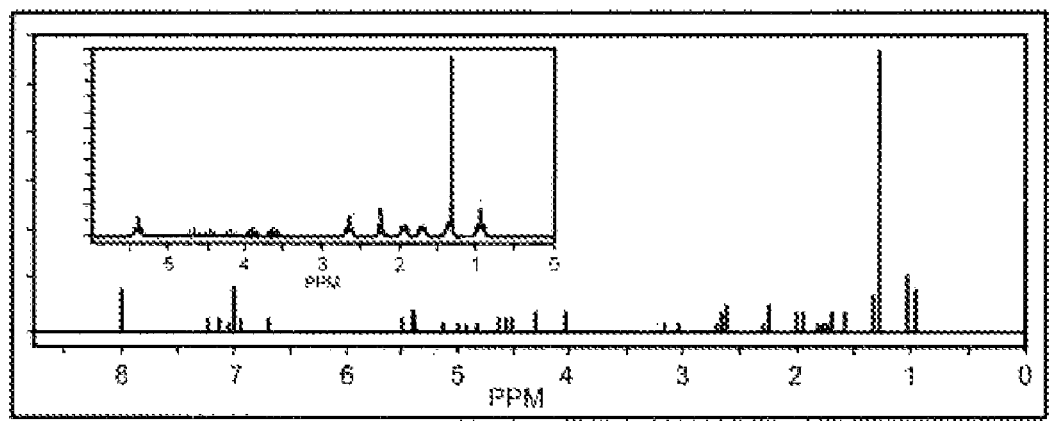

Approximately 20 mg of purified PDAG was dissolved in d6-DMSO and the spectrum acquired in a NITY Plus-400 nuclear magnetic resonance spectrometer ($^1$H at 399.95 MHz). The radio frequency band width was 6000 Hz with a pulse angle of 45 degrees, a relaxation time of 1.0 seconds and an acquisition time of 2.601 seconds/scan. The total analysis time was 11 hours, 43 minutes, and 22 seconds. Several key structural features are revealed. Beginning with the low field region of the spectrum an acidic proton absorbance is observed at 9.2 ppm. The aromatic region reveals a large multiplet centered around 8.0 ppm characteristic of the hydrogens of the peptidyl amide. Another split multiplet is observed centered at 7.4 ppm (J=200 Hz) that may indicate the presence of phenylalanine and/or tyrosine. Vinylic hydrogens are observed in the region of 6.6-7.0 ppm that could be accounted for by an unsaturated fatty acid. Methyl hydrogen absorbance observed at 0.8 ppm and significant methylene hydrogen absorbance is noted in the region around 1.5 ppm. Extensive conjugation of the peptide with fatty acids could also account for the broadening of the aromatic signals that could arise from anisotropic shielding effects of the methyl and methylene protons. The broad signals in the 4.0-5.0 ppm region are consistent with the absorbance of the α-methylene hydrogens of a peptide bond. FIG. 2 presents the NMR spectrum of the HPLC purified PDAG (FIG. 2A) as compared to the theoretically predicted NMR of a model 1-peptidyl-2,3-diacylglyceride (FIG 2B). The insert shows the actual NMR spectra of 1-stearoyl-2-arachidonoyl glycerol. The predicted $^1$H chemical shifts (FIG. 2B) relative to trimethylsilane of a hypothetical 1-peptidyl-2,3-diacylglyceride are based upon the lowest energy conformation of derived from the theoretical calculation of energy minimization of the heat of formation and steric energies using repetitive iterations of semiempirical MNDO calculations (MOPAC and MM2). The good agreement between the theoretically predicted NMR of a model 1-peptidyl-2-arachidonoyl-3-stearoyl and the naturally occurring PDAG supports this structural characterization.

Figure 3:
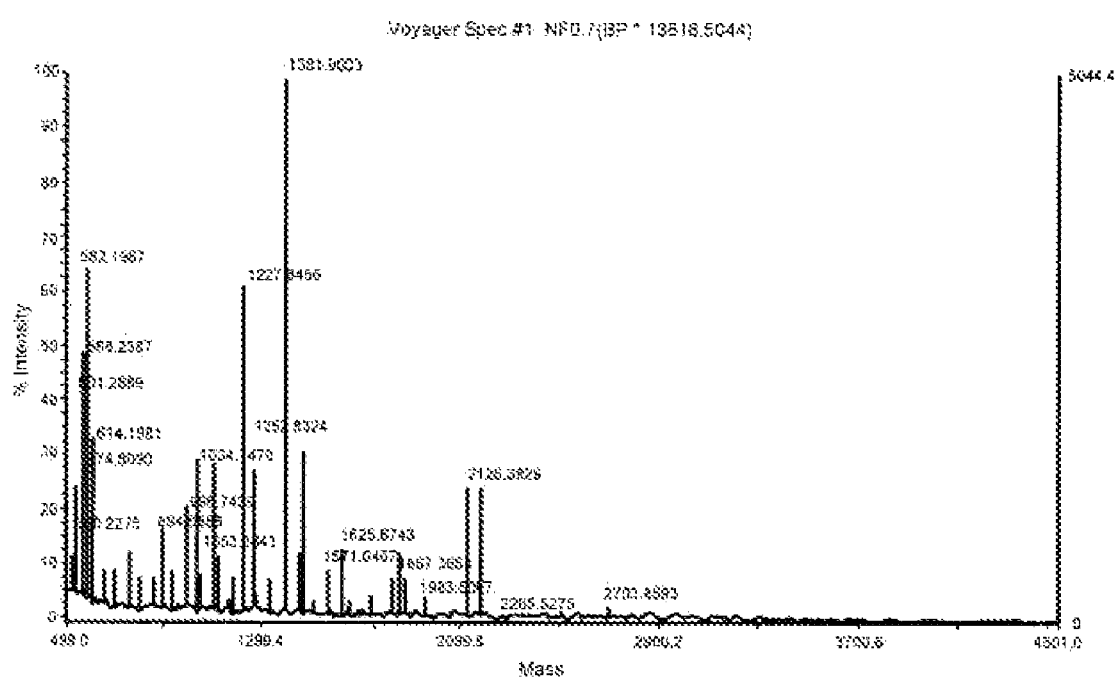
FIG. 3 shows a MALDI-TOF spectrum of non-primate 1-peptidyl-2,3-diacylglyceride.

MALDI-TOF mass spectrometry of the non-primate PDAG is presented in FIG. 3. Table 2 shows the relationship and identity of the major ion fragments and demonstrates the amino acid composition of the peptidyl moiety of PDAG.

TABLE 2

MALDI-TOF MS Ion Relationships

| Ion 1 | Ion 2 | Difference | Identity |
| --- | --- | --- | --- |
| 1734 | 1571 | 163 | Tyrosine (—H$_2$O) |
| 1625 | 1469 | 156 | Arginine (—H$_2$O) |

TABLE 2-continued

MALDI-TOF MS Ion Relationships

| Ion 1 | Ion 2 | Difference | Identity |
|---|---|---|---|
| 1571 | 1469 | 102 | Threonine (—OH) |
| 1469 | 1382 | 87 | Serine (—H$_2$O) |
| 1382 | 1253 | 129 | Lysine (—OH) |
| 1382 | 1228 | 154 | Hisitidine (—H) |
| 1228 | 1113 | 115 | Asparagine (—OH) |
| 1113 | 999 | 114 | Leucine (—OH) |
| 999 | 895 | 104 | Cysteine (—OH) |
| 895 | 592 | 303 | Arachidonate (—H) |

The foregoing is consistent with peptide fragments of sequence RSHNLCX (1625 amu) (SEQ ID NO 2)and YTSHNLCX (1734 amu) (SEQ ID NO 3)where X has an ion mass of 879 and 880 amu, respectively.

The MALDI ions at 727 and 895 amu contain a diacylglycerol phosphate moiety consistent with 1-stearoyl-2-arachidonoyl-3-phosphoglycerol (727 amu) and the ion at 895 is consistent with 1-argininephospotidyl-2-arachidonoyl-3-stearoyl glycerol. Thus, a partial structure for the bioactive PDAG from non-primate serum is consistent with the sequence YTSHNLCXCLNHSR-OPO$_3$-DAG (SEQ ID NO 6). As such the peptidyl moiety would be classified as a cytokine of the CXC type.

EXAMPLE 2

Figure 4A:
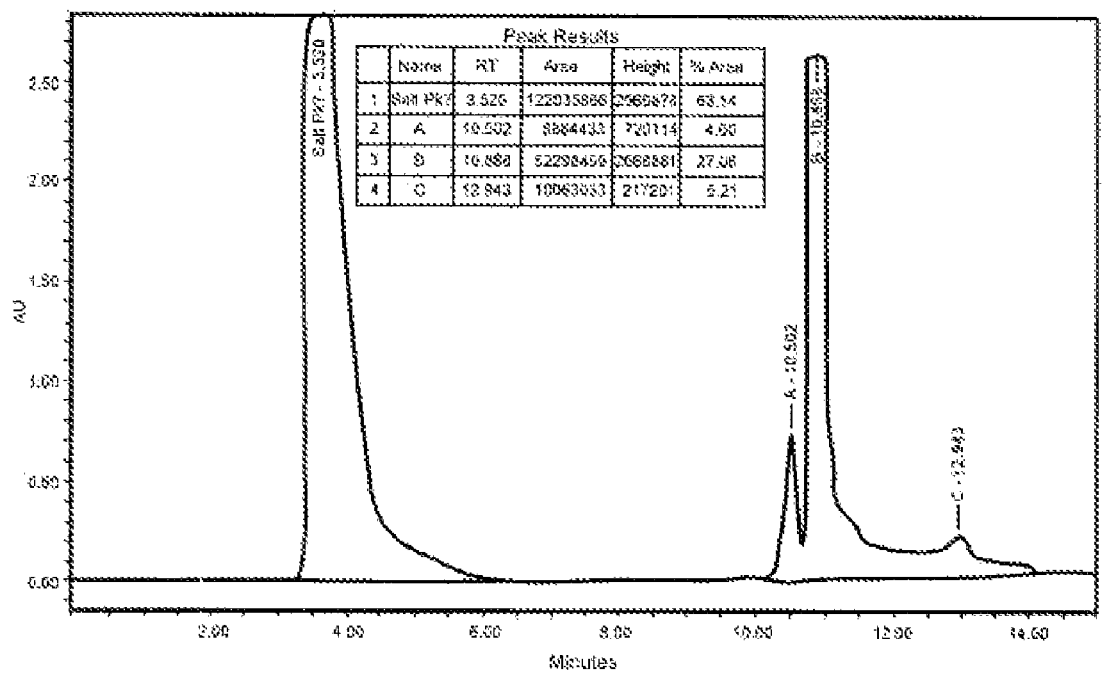
FIG. 4 shows an HPLC chromatogram of human serum fraction containing 1-peptidyl-2,3-diacylglyceride before (FIG. 4A) and after (FIG. 4B) treatment with lipoprotein lipase.
Figure 4B:
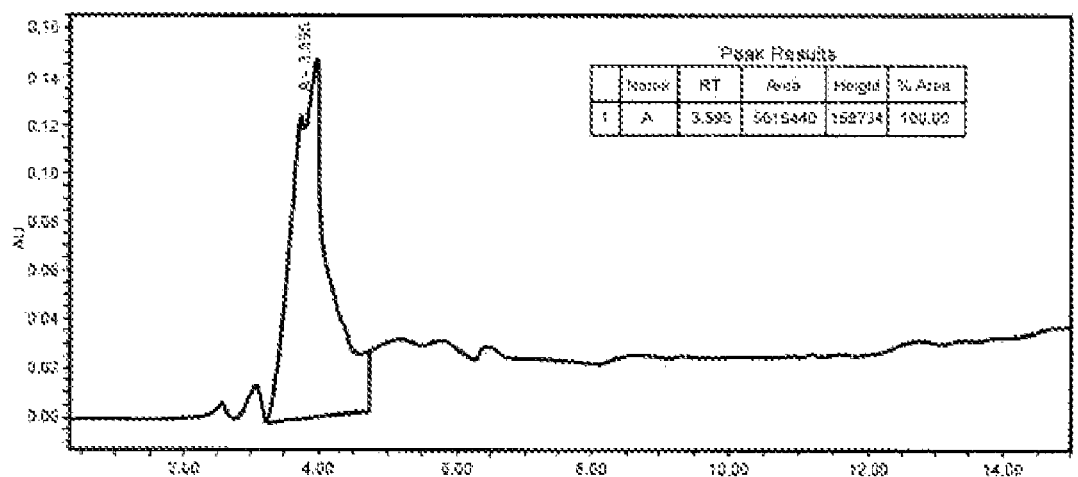

This example describes the cleavage of PDAGs in the presence of lipoprotein lipase to release the peptide portion of the molecule. Two separate pooled venous blood samples (30 ml each) were collected from seven cynomologous monkeys (Macaques) at the Primate Biomedical Research Center of the University of Illinois at Chicago College of Medicine. Pooled human venous blood samples (500 ml) were procured from Lampire Biological Laboratories, Inc. Lipoprotein lipase (purified from bovine milk, Sigma-Aldrich) was added to one of the monkey blood samples and both were allowed to coagulate, contrifuged, and the serum fraction collected, frozen, and stored (−80° C.) prior to shipment to the Molecular Medicine Institute at the University of Pittsburgh. PDAGs were isolated and analyzed by the procedure described in Example 1. The PDAG fraction from normal monkey serum eluted at nominally 21 minutes under the specified conditions and the MALDI-TOF MS confirmed the presence of the 1-peptidyl-2,3-diacylglyceride and the corresponding peptide and 1-stearoyl-2-arachidonoyl glycerol fragments. In contrast only the PDAG peptide was found in the serum fraction that was prepared in the presence of lipoprotein lipase. Similar results were obtained using pooled human serum. The HPLC profiles of human serum before and after lipoprotein lipase treatment are presented in FIG. 4. Analytical HPLC was performed using a Phemomenex C-18 column (250×4.6 mm) and a mobile phase 0.1% aqueos TFA (solvent A) and acetonitrile in 0.1% aqueous TFA (solvent B). A linear gradient was formed starting from 95% A and 5% B to 20% A and 80% B over 15 minutes (5% per minute). Under these conditions the PDAGs from human, monkey, and non-primate serum are chromatographically indistinguishable and elute between 10-11 minutes.

EXAMPLE 3

Figure 5A:
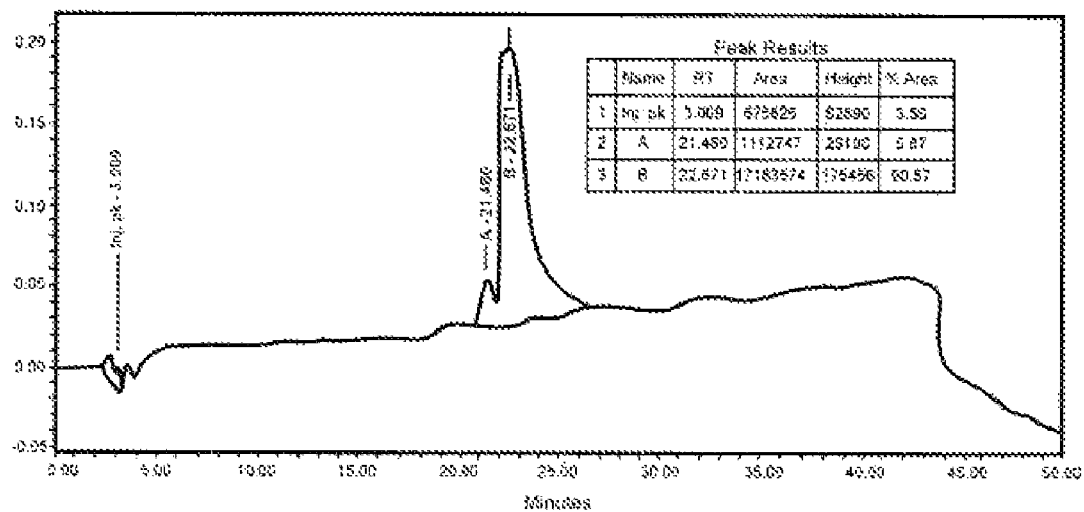
FIG. 5 shows an HPLC chromatogram of purified monkey serum containing 1-peptidyl-2,3-diacylglyceride (FIG. 5A) and the corresponding fraction from monkey plasma (FIG. 5B).
Figure 5B:
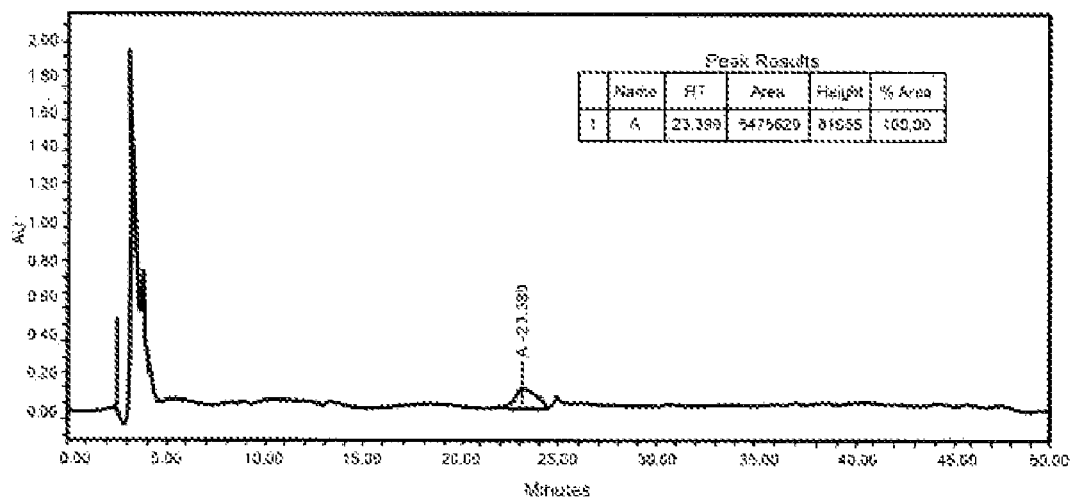

This example establishes that PDAGs are induced from platelets during the coagulation process of whole blood. Pooled venous blood samples (30 ml each) were collected from seven cynomologous monkeys (Macaques) at the Primate Biomedical Research Center of the University of Illinois at Chicago College of Medicine with and without sodium heparin added as an anticoagulant. The plasma and serum fractions were collected after centrifugation, frozen, and stored (−80° C.) prior to shipment to the Molecular Medicine Institute at the University of Pittsburgh. The plasma and serum was analyzed by the procedure described in Example 1. The PDAG present in plasma was only 2% of that found in serum. The MALDI-TOF MS confirmed the presence of the 1-peptidyl-2,3-diacylglyceride and the corresponding peptide and 1-stearoyl-2-arachidonoyl glycerol fragments. A comparison of the HPLC profiles of PDAG isolated from monkey serum and plasma is presented in FIG. 5. Analytical HPLC was performed using a Phemomenex C-18 column (250×4.6 mm) and a mobile phase 0.1% aqueos TFA (solvent A) and acetonitride in 0.1% aqueous TFA (solvent B). A linear gradient was formed starting from 95% A and 5% B to 70% A and 30% B over 10 minutes (2.5% per minute) and then to 40% A and 60% B over the next 30 minutes (1 per minute). Under these conditions the PDAG from monkey serum elutes at 22.7 minutes.

EXAMPLE 4

This example describes the method for solid phase synthesis of the peptidyl portion of the PDAGs and the preparation of fluorescently labeled PDAGs or PDAG peptides. Synthesis of PDAG peptide and variants is accomplished by the solid-phase on 433A peptide synthesizer (Applied Biosystems, Foster City, Calif.) using FMOC synthesis protocol with extended HBTU/HOBt coupling cycles and pre-loaded Wang resins. Following the synthesis, cleavage of the peptide side chain protective groups and release from the resin with Reagent-K will be followed by diethyl ether extraction and lyophilization. Reversed Phase C-18 purification of the resultant crude peptides on a Waters DeltaPrep 4000 chromatography system is followed by MALDI-TOF characterization on an Applied Biosystems Voyager-DE Biospectometry workstation to confirm the amino acid sequence.

Phycoerythrin (PE) is a red fluorescing dye and Fluorceinisethiocynate (FITC) is a green fluorescing dye that are commercially available in an activated form for conjugation to primary amines and sulfhydryls. PE (or FTIC) is conjugated through a spacer arm to the N-terminus of the peptidyl portion of PDAG. In facilitate conjugation through the N-terminus, PDAG peptide is activated by attachment of the thiol reactive extended-chain analogue of succinimidyltrans-4-(maleimidylmethyl)cyclohexane-1-carboxylate(LC-SMCC). Separation of unreacted LC-SMCC from the derivatized PDAG peptide is accomplished by elution from G-10 columns with phosphate buffered saline (PBS). Activation of the pyridyldisulfide derivative of R-Phycoerythrin (or FITC) to the free thiol form occurs after a 10-15 minute incubation with tris-(2-carboxyethylphosphine (TCEP). Immediately combining the purified LC-SMCC PDAG peptide derivative with activated R-Phycoerythrin (or FITC) is followed by mixing at 4° C. overnight. After the incubation period is complete, the reaction is stopped by the addition of N-ethyl maleimide (NEM) which caps any remaining thiol groups. Purification of the R-Phycoerythrin (or FITC)-PDAG conjugate on G-10 columns is accomplished by elution with PBS and overnight lyophilization, which yields the final product.

EXAMPLE 5

This example establishes the bioequivalence of the PDAGs isolated from primate and non-primate species with a synthetic peptide reference standard (FNN-21). FNN-21 is the 21 amino acid peptide in tetanus toxin that is the putative universal T-cell epitope (aa's 947-967 of tetanus toxin). Seven groups of 3 rabbits each recieved either: (i) normal saline placebo, (ii) Freund's Complete Adjuvant (FCA), (iii) monkey PDAG serum factor (95+% purity by HPLC), (iv) goat PDAG serum factor (95+% purity by HPLC), or one of four synthetic FNN-21 doses (25 µg, 50 µg, or 100 µg). Arterial blood samples were drawn from each animal, coagulated, and the serum analyzed for IgM titer by ELISA.

The PDAG from serum (95+% purity) was prepared as described in Example 1. Synthetic FNN-21 was prepared by a standard FMOC solid phase peptide synthesis protocol using extending HBTU/HOBt coupling cycles and pre-loaded Wang resins. All test articles were formulated for injection in Freund's Complete Adjuvant (FCA).

Synthetic FNN-21 was dissolved in normal saline to give a final concentration of 1 mg/ml. This stock inoculate was diluted 1:2.5, 1:5, or 1:10 with FCA to give 400 µg/ml, 200 µg/ml, and 100 µg/ml inoculates respectively.

Purified serum derived PDAG was dissolved in normal saline to give a 1 mg/ml stock inoculate. This stock inoculate was diluted 1:5 with FCA to give a final inoculate concentration of 200 µg/ml.

On day 0 of the study all rabbits received 0.25 ml of the appropriate inoculate or normal saline placebo by sub-cutaneous injection in the lateral thorax. Arterial blood samples were drawn from all animals on Day -1 (baseline) and on Days 3, 5, 7, 10, and 14 and allowed to coagulate. The serum was analyzed for immunoglobulin titers (IgG and IgM) specific for *M. tuberculosis* by ELISA methods and are reported as the average absorbance from duplicate measurements of each of the three rabbits in each test group (n×6) in absorbance units (AU 405 nm) for each analysis day. These results are presented in the following table. The FNN-21 test results are for the highest dose test group (100 µg).

TABLE 3

Bioequivalence of PDAGs

|  | Day 1 | Day 3 | Day 5 | Day 7 | Day 10 | Day 14 |
| --- | --- | --- | --- | --- | --- | --- |
| Normal Saline | 0.12 | 0.16 | 0.14 | 0.14 | 0.14 | 0.14 |
| FCA | 0.10 | 0.12 | 0.16 | 0.20 | 0.26 | 0.36 |
| FNN-21 | 0.14 | 0.15 | 0.13 | 0.16 | 0.25 | 0.35 |
| Primate PDAG | 0.14 | 0.23 | 0.42 | 0.65 | 0.91 | 1.08 |
| Non-primate PDAG | 0.12 | 0.20 | 0.43 | 0.63 | 0.93 | 1.13 |

EXAMPLE 6

This example demonstrates that PDAG is not intrinsically antimicrobial. PDAG (200 µg/ml) was assessed for antimicrobial activity against both gram positive and gram negative bacteria by performing disk agar diffusion assays as described in Hart and Champlin (1988). Antibiotic minimum inhibitory concentrations (MICs) were determined in Mueller-Hinton broth using the broth dilution method described previously (Darnell et al., 1987). Sterile filter paper disks impregnated with PDAG were aseptically applied to the seeded plate surfaces. The plates were incubated for 24 h at 37° C., during which time inhibition of growth in areas surrounding the disks were visually assessed at 4 and 24 h. PDAG failed to inhibit the growth of all test bacteria species.

PDAG was unable to inhibit growth of gram-negative and gram-positive bacteria. The minimum inhibitory concentration (MIC) for a typical defensin is usually in the range of 1 to 8 µg/ml. PDAG was tested at 200 µg/ml, 25× the upper MIC range recognized for defensins and 4× the observed therapeutic dose, with no inhibition of either gram positive or gram negative bacteria growth.

EXAMPLE 7

This example demonstrates the prophylactic benefit of PDAG and establishes the clearance rate of PDAG to a no effect level (NOEL). A single dose of PDAG at the therapeutic level (50 µg, sub. cu.) was administered to mice at various times prior to receiving a lethal bacterial challenge and the morbidity/mortality in each group was followed for ten days. PDAG was administered 1, 2, and 4 days prior to challenge (days -1, -2, and -4), or coincident with the challenge on day 0. Onset of mortality was observed by day 4 in control populations of female Swiss Webster mice challenged with *S. typhimurium* (~5×10$^3$ cfu/mouse administered i.p.). A rapid rise in death ensued with a cumulative mortality of approximately 80% by 7-8 days post challenge and 100% mortality by day 10. Mice treated with PDAG four days prior to challenge showed no significant difference in mortality from the untreated control mice. Prophylactic benefit, however, was observed if PDAG was given on days -2, -1, or 0. By day 8 the untreated control population reached 80% mortality, while groups that received PDAG on either days -2, -1, or 0 had cumulative mortality rates of 60%, 30%, and 50%, respectively. Beginning with day 4 post-challenge (when mortality was established in this control population) there was a statistically significant delay in onset of mortality between the control group and the PDAG treated groups. The day -1 treatment group also had significantly lower cumulative mortality by day 8 than the day 0 and day -2 populations (p=0.0189 and p=0.0012 respectively). Therefore, PDAG clearance rate to a NOEL is 96 hours and the 50% clearance rate of PDAG is approximately 48 hours.

EXAMPLE 8

This example examines acute phase protein production as an indicator of the pro-inflammatory actions of PDAG in naive Sprague Dawley rats. PDAG was administered at either the therapeutic dose (50 µg, i.v.) or 2× the therapeutic dose (100 µg, i.v.) in two groups of 5 rats. A placebo group of 5 rats received normal saline. Rats were sacrificed three days later and the circulating acute phase proteins (serum amyloid A and haptoglobin) were measured in the blood taken by cardiac aspiration. The average acute phase protein concentrations are depicted in Table 4 below.

TABLE 4

Day 3 Acute Phase Protein Levels

|  | Placebo | 50 µg Dose | 100 µg Dose |
| --- | --- | --- | --- |
| Serum Amyloid A (mg/ml) | 0.006 | 3.230 | 5.617 |
| Haptoglobin (mg/ml) | 0.0410 | 5.312 | 7.841 |

These results clearly demonstrate the pro-inflammatory effect of PDAG as measured by induced acute phase protein production and that the acute phase protein production appears to be PDAG dose dependent.

EXAMPLE 9

This example establishes the efficacy of PDAG for treatment of lactating dairy cows that are diagnosed with clinical and sub-clinical bacterial mastitis. The efficacy of PDAG treatment of bovine mastitis was examined in a 250-head commercial dairy. The average bulk tank somatic cell count (BTSCC) for the herd was 763,000 during the testing period with nearly 40% of the herd having above normal somatic cell counts. Forty-nine animals (n=49) with an elevated somatic cell count and not undergoing treatment were randomly selected and treated with PDAG (600 µg, i.m.) followed by a second booster injection three days after the initial dose. The remainder of the herd (n=100), excluding animals undergoing treatment, were left untreated as a control group. The somatic cell count (SCC) of the treatment group animals and the control animals were compared thirty days later after the next DHIA somatic cell count measurement was taken. The test and control groups were determined not to be statistically different prior to treatment (t=0.1703, P=0.8650). After treatment fifty-six percent (56%) of the animals in the PDAG treatment group showed a decreased SCC with an average SCC decrease of 25% per animal while the average SCC in the untreated control animals increased by 11% per animal over the test period. This difference was determined to be statistically significant (P<0.05).

Nineteen animals were showing signs of clinical mastitis, i.e. abnormal milk appearance. These animals were randomly assigned to either a test or a control group. The control group animals (n=10) were treated according to the dairy's normal practice for treatment of clinical cases of mastitis, i.e. intramuscular injection of Polyflex brand (Fort Dodge Animal Health) of ampicillin (5mg/lb×3 days). The test group (n=9) animals were treated with PDAG (600 µg, i.m.) followed by a booster injection three days later. The SCC's for the treatment and control animals were compared after the next DHIA somatic cell count measurement was taken. The means of the pre-treatment test and control groups were determined to not be statistically different (P=0.3965, t=0.8696) and neither were the standard deviations of the two groups statistically different (F=1.889, P=0.1914). That the sampled data was derived from a population that followed a Gaussian distribution was tested by the Kolmogorov and Smirnov method and determined be a normal distribution (KS~0.2, P>0.01). Seven animals in the test group showed improvement and the average SCC for the group declined by 19%. Two animals in the test group were refractory to treatment. Only one animal in the control group showed improvement and the average somatic cell count for the control group increased by 7% during the test period. These results are tabulated below in Table 5.

TABLE 5

Efficacy of PDAG as Compared to Conventional Antibiotic Treatment

| Animal ID | Somatic Cell Count | |
|---|---|---|
| | Day 0 | Day 30 |
| PDAG Test Group | | |
| 11 | 1119 | 7981 |
| 15 | 1800 | 753 |
| 40 | 3310 | 322 |
| 95 | 2740 | 282 |
| 116 | 3581 | 4154 |

TABLE 5-continued

Efficacy of PDAG as Compared to Conventional Antibiotic Treatment

| Animal ID | Somatic Cell Count | |
|---|---|---|
| | Day 0 | Day 30 |
| 129 | 1008 | 247 |
| 214 | 1759 | 198 |
| 220 | 3209 | 1029 |
| 230 | 1056 | 816 |
| Antibiotic Control Group | | |
| 3 | 2136 | 1879 |
| 13 | 3869 | 3486 |
| 32 | 5046 | 5863 |
| 41 | 2636 | 2143 |
| 99 | 1502 | 220 |
| 117 | 2400 | 8147 |
| 168 | 1777 | 2025 |
| 215 | 4851 | 1748 |
| 224 | 1717 | 2519 |
| 232 | 877 | 563 |

Nine animals in the herd were historically refractory to antibiotic treatment or had multiple incidences of clinical mastitis while in milk. These nine animals plus the two refractory animals (Animal #s 11 and 116) from the PDAG Test Group were grouped together (n=11) for treatment with antibiotic (Polyflex) plus PDAG as an adjunctive therapeutic. After the next scheduled DHIA SCC measurement, the treatment efficacy was evaluated. Eight of the 11 animals improved (80%) with a 42% decrease in this group's average SCC. Two animals (20%) remained refractory to treatment. These results are tabulated below in Table 6.

TABLE 6

Efficacy of PDAG as an Adjunctive Therapeutic

| Animal ID | Somatic Cell Count | |
|---|---|---|
| | Day 0 | Day 30 |
| 11 | 7981 | 3314 |
| 20 | 913 | — |
| 46 | 1282 | 505 |
| 49 | 1563 | 4807 |
| 58 | 9036 | 249 |
| 67 | 3614 | 2285 |
| 91 | 7802 | 660 |
| 116 | 4154 | 2929 |
| 220 | 1029 | 4338 |
| 137 | 1204 | 1164 |
| 213 | 1762 | 978 |

Note:
Animal #20 entered dry off prior to the end of the test period.

We identified 5 sub-clinical case of mastitis in the herd. Bacterial cultures of the milk from these five animals showed a mixture of non-hemolytic *Streptococcus* and *E. coli* as the causative organisms. These five sub-clinical animals were treated with PDAG and the SCC's were measured at the next DHIA sampling interval after treatment. Four of the five animals had SCC's that were normal after treatment and all five animals showed improvement. The average SCC for this group before treatment was 715,000 and after treatment declined to 205,000. A two-tailed t-test for significance with Welch's approximation to correct for the unequal standard deviations indicated that the difference in the means of the pre-treatment and post-treatment groups was very significant (P=0.005, t=4.759). The results are presented below in Table 7.

TABLE 7

Efficacy of PDAG for the Treatment of Sub-Clinical Mastitis.

| | Somatic Cell Count | |
|---|---|---|
| Animal ID | Day 0 | Day 30 |
| 90 | 419 | 113 |
| 192 | 619 | 232 |
| 147 | 866 | 232 |
| 171 | 994 | 125 |
| 81 | 675 | 323 |

I claim:

1. A method of stimulating an immune response in a subject in need thereof comprising:

administering an effective amount of an agent comprising a peptidyl glyceride of formula (I):

$$\begin{array}{l} CH_2-O-X_1 \\ HC-O-X_2 \\ CH_2-O-X_3 \end{array} \quad (I)$$

wherein $X_1$ is a peptide of amino acid sequence YTSHNLCXCLNHSR (SEQ ID NO: 4) wherein X can be any natural amino acid attached to the glyceride (I) to form an ester with the C-terminal arginine (R), $X_2$ is arachidonoyl, and $X_3$ is stearoyl; and stimulating an immune response in the subject.

2. The method of claim 1, wherein stimulating an immune response further comprises stimulating an innate immune response.

3. The method of claim 1, wherein stimulating an immune response further comprises stimulating tissue resident immune cells.

4. The method of claim 3, wherein the tissue resident immune cells are selected from γδ T cells, monocytes, NK cells, neutrophils, CD5+ B-cells and combinations thereof.

5. The method of claim 3, wherein the tissue resident immune cells are stimulated when contacted by the peptide.

6. The method of claim 1, wherein stimulating an immune response comprises stimulating an immune response for at least about 3 days following administration.

7. The method of claim 1, wherein the compound is substantially deposited in a fatty tissue of the subject.

8. The method of claim 1, wherein administrating the agent comprises administering the agent by a method selected from enteral, parenteral, topical, mammary infusion and combinations thereof.

9. The method of claim 1, wherein the agent is administered prior to exposure to a disease forming agent.

10. The method of claim 6, wherein infection is substantially prevented.

11. The method of claim 1, wherein the agent is administered prior to infection.

12. The method of claim 1, wherein the agent is administered following exposure to a disease forming agent.

13. The method of claim 1, wherein the agent is administered following infection.

14. A compound comprising a peptide of amino acid sequence YTSHNLCXCLNHSR (SEQ ID NO: 4) or an inversion thereof, wherein X can be any natural amino acid.

15. The compound of claim 14, wherein the peptide is covalently attached to a lipid.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Xaa Ser His Asn Leu Cys Xaa
1               5

<210> SEQ ID NO 2
<211> LENGTH: 7
<212> TYPE: PRT
<213> ORGANISM: Artificial
<220> FEATURE:
<223> OTHER INFORMATION: Synthesized peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 2

Arg Ser His Asn Leu Cys Xaa
1               5

<210> SEQ ID NO 3
<211> LENGTH: 8
<212> TYPE: PRT
<213> ORGANISM: Artificial
<220> FEATURE:
<223> OTHER INFORMATION: Synthesized peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 3

Tyr Thr Ser His Asn Leu Cys Xaa
1               5

<210> SEQ ID NO 4
<211> LENGTH: 14
<212> TYPE: PRT
<213> ORGANISM: Artificial
```

```
<220> FEATURE:
<223> OTHER INFORMATION: Synthesized peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 4

Tyr Thr Ser His Asn Leu Cys Xaa Cys Leu Asn His Ser Arg
1               5                   10

<210> SEQ ID NO 5
<211> LENGTH: 21
<212> TYPE: PRT
<213> ORGANISM: Artificial
<220> FEATURE:
<223> OTHER INFORMATION: Synthesized peptide

<400> SEQUENCE: 5

Phe Asn Asn Phe Thr Val Ser Phe Trp Leu Arg Val Pro Lys Val Ser
1               5                   10                  15

Ala Ser His Leu Glu
            20

<210> SEQ ID NO 6
<211> LENGTH: 14
<212> TYPE: PRT
<213> ORGANISM: Artificial
<220> FEATURE:
<223> OTHER INFORMATION: Synthesized peptidyl diacylglycerol
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: peptidyl-linked diacylglycerol modification

<400> SEQUENCE: 6

Tyr Thr Ser His Asn Leu Cys Xaa Cys Leu Asn His Ser Arg
1               5                   10
```